US008630387B2

(12) United States Patent
Geiger et al.

(10) Patent No.: US 8,630,387 B2
(45) Date of Patent: Jan. 14, 2014

(54) METHOD FOR RECORDING AN X-RAY IMAGE AND X-RAY SYSTEM

(75) Inventors: Bernhard Geiger, Buekenhof (DE); Rainer Kaltschmidt, Oberschöllenbach (DE); Peter Scheuering, Fürth (DE); Markus Schild, Herzongenaurach (DE)

(73) Assignee: Siemens Aktiengesellschaft, Munich (DE)

( * ) Notice: Subject to any disclaimer, the term of this patent is extended or adjusted under 35 U.S.C. 154(b) by 338 days.

(21) Appl. No.: 13/092,349

(22) Filed: Apr. 22, 2011

(65) Prior Publication Data

US 2011/0261930 A1    Oct. 27, 2011

(30) Foreign Application Priority Data

Apr. 23, 2010    (DE) .......................... 10 2010 018 045

(51) Int. Cl.
*G01N 23/04* (2006.01)

(52) U.S. Cl.
USPC ............................................. 378/62; 378/98

(58) Field of Classification Search
USPC .......................................... 378/62, 19, 98, 91
See application file for complete search history.

(56) References Cited

U.S. PATENT DOCUMENTS

2004/0218729 A1* 11/2004 Xue et al. ....................... 378/210
2005/0058251 A1    3/2005 Spahn ........................... 378/114

FOREIGN PATENT DOCUMENTS

DE    10334395 A1    3/2005    ............. H05G 1/60

OTHER PUBLICATIONS

Groh, B. et al., "Photo Diode Gain Calibration of Flat Dynamic X-ray Detectors Using Reset Light", Medical Imaging 2002: Physics of Medical Imaging; Proceedings of the SPIE, vol. 4682, pp. 438-446.
Mail, N. et al., "Lag Correction Model and Ghosting Analysis for an Indirect-Conversion Flat-Panel Imager", Journal of Applied Clinical Medical Physics, vol. 8, No. 3, pp. 137-146.
German Office Action, German patent application No. 10 2010 018 045.9-54, 4 pages.

* cited by examiner

*Primary Examiner* — Hoon Song
(74) *Attorney, Agent, or Firm* — King & Spalding L.L.P.

(57) ABSTRACT

In order to optimize the recording time, provision is made of a method for recording an X-ray image using an X-ray system with an X-ray detector, an X-ray source, a system control, and a computational unit, wherein information relating to the relative direct radiation component in a reference X-ray image and information relating to the utilized recording geometry and/or the utilized primary X-ray dose and/or the utilized filtering is used to determine a relaxation time, during which a ghosting effect of the X-ray detector resulting from a preceding X-ray image decays at least in part, which relaxation time is adapted to the X-ray image to be recorded, and the determined relaxation time is utilized to actuate the recording of the X-ray image.

19 Claims, 2 Drawing Sheets

METHOD FOR RECORDING AN X-RAY IMAGE AND X-RAY SYSTEM

CROSS-REFERENCE TO RELATED APPLICATIONS

This application claims priority to DE Patent Application No. 10 2010 018 045.9 filed Apr. 23, 2010. The contents of which are incorporated herein by reference in its entirety.

TECHNICAL FIELD

The invention relates to a method for recording an X-ray image and to an X-ray system for carrying out such a method.

BACKGROUND

All digital image convertors in the field of radiology (e.g. image amplifiers, flat-panel detectors with indirect or direct conversion, etc.) convert imaging X-ray quanta into digital grayscale values via various intermediate steps. In the process, the corresponding convertor layers of the image convertor filter an inherently stochastic radiation field from an X-ray tube and convert a radiation field, which has been attenuated in a modulated fashion by an examination object (e.g. a patient), into a diagnosable X-ray image within the scope of DQE (detective quantum efficiency). During the scope of these different conversion types, systematic and stochastic artifacts are always introduced as well into the useful signal and should be minimized as far as possible. In this context, the so-called "ghosting" is a known phenomenon. Part of the image signal of the preceding X-ray image remains in the memory of the detector and thus contributes to the useful signal of the subsequent X-ray image in an additive fashion. This in turn is expressed occasionally by distracting artifacts, which can moreover result in a misdiagnosis.

According to the prior art, there are a number of different approaches for tackling the problem of ghosting: By selecting suitable layer thicknesses and layer designs of e.g. a scintillator (convertor layer), it is possible to make a compromise between resolution on the one hand and the tendency for ghosting on the other hand. Additionally, a so-called reset light can be utilized for partial deletion of the detector memory, as disclosed in e.g. "Photodiode gain calibration of flat dynamic x-ray detectors using reset light" by Burkhard A. Groh, Bernhard Sandkamp, Mathias Hoernig, Volker K. Heer, Falko Busse and Thierry Ducourant, Proc. SPIE, vol. 4682, pages 438 to 446, Medical Imaging 2002: Physics of Medical Imaging, Larry E. Antonuk; Martin Yaffe; Eds. Within the scope of digital image processing, it is possible to undertake image data correction by means of a suitable model function using e.g. the knowledge of the physical causes of the ghosting, which image data correction re-subtracts contrast-rich ghosts in particular from the X-ray image; this is known from, for example, "Lag correction model and ghosting analysis for an indirect-conversion flat-panel imager" by Noor Mail, Peter O'Brien and Geordi Panga, Journal of Applied Clinical Medical Physics, Vol. 8, No. 3, 2007, pages 137 to 146.

Due to their physical causes, the ghosting effects relax relatively quickly, and so a further method for preventing these artifacts is to plan for sufficient time between two recordings. To this end, a system computer in modern X-ray image systems prescribes a fixed mandatory pause, during which no further images can be taken. Furthermore, methods are also known, for example, in which a so-called de-ghost scan with a very high dose and a clear beam path leads to artificial overloading of the detector, and this produces a homogeneous, ghost-free empty image.

SUMMARY

According to various embodiments, a simple method can be provided that allows a largely ghost-free X-ray image to be recorded. Moreover, according to other embodiments, an X-ray system can be provided suitable for carrying out the method.

According to an embodiment, a method for recording an X-ray image using an X-ray system, comprising an X-ray detector, an X-ray source, a system control, and a computational unit, wherein information relating to the relative direct radiation component in a reference X-ray image and information relating to the recording geometry utilized for the reference X-ray image and/or the primary X-ray dose utilized for the reference X-ray image and/or the filtering utilized for the reference X-ray image is used to determine a relaxation time, during which a ghosting effect of the X-ray detector resulting from a preceding X-ray image, more particularly the reference X-ray image, decays at least in part, which relaxation time is adapted to the X-ray image to be recorded, and the determined relaxation time is utilized to actuate the recording of the X-ray image.

According to a further embodiment, information relating to the X-ray detector can be likewise used for determining the adapted relaxation time. According to a further embodiment, the information can be evaluated by means of the computational unit and the adapted relaxation time is calculated therefrom. According to a further embodiment, the adapted relaxation time can be utilized as the pause between the recording of two X-ray images, more particularly between the recording of the preceding X-ray image and the X-ray image to be recorded.

According to a further embodiment, an evaluation of the reference X-ray image in respect of direct radiation components can be utilized to determined the adapted relaxation time. According to a further embodiment, the reference X-ray image can be formed by the respective preceding X-ray image. According to a further embodiment, the information relating to the primary X-ray dose from the X-ray source may comprise a tube voltage and/or a current-time product. According to a further embodiment, the information relating to the recording geometry may comprise a distance between the X-ray detector and the focus of the X-ray source and/or a central beam angle. According to a further embodiment, the information relating to the filtering may comprise an attenuation factor of an anti-scatter grid and/or a filter. According to a further embodiment, the information relating to the X-ray detector may comprise a specific lag property of the X-ray detector. According to a further embodiment, the adapted relaxation time t can be calculated using the formula $$t \propto D \oplus r_D \otimes l,$$

where D is the detector dose, $r_D$ is the relative direct radiation component of the reference X-ray image, and l is the specific lag property of the X-ray detector. According to a further embodiment, the detector dose can be calculated using the formula $$D \propto kV_p \oplus mAs \otimes gr \otimes fi \otimes ffA \otimes \alpha,$$

where $kV_p$ is the tube voltage of the X-ray source, mAs is the current-time product of the X-ray source, gr is the grid factor of a grating, fi is the filter factor of a filter, ffA is the distance between the X-ray detector and the focus of the X-ray source, and α is the central beam angle. According to a further embodiment, a relaxation time can be determined, during which a ghosting effect of the X-ray detector decays by at least 50%, more particularly by 90%.

According to another embodiment, an X-ray system for carrying out the above method may comprise an X-ray detector, an X-ray source, a system control, and a computational unit, wherein the computational unit is embodied to determine a relaxation time, during which a ghosting effect of the X-ray detector resulting from a preceding X-ray image decays at least in part, using information relating to the relative direct radiation component in a reference X-ray image and information relating to the recording geometry utilized for the reference X-ray image and/or the utilized primary X-ray dose and/or the utilized filtering, which relaxation time is adapted to the X-ray image to be recorded, and the system control is embodied to utilize the determined relaxation time for actuating the recording of the X-ray image.

BRIEF DESCRIPTION OF THE DRAWINGS

The invention and further embodiments as per the features of the dependent claims are explained in more detail below on the basis of schematically illustrated exemplary embodiments, shown in the drawing, without this restricting the invention to these exemplary embodiments. In the drawing:

DETAILED DESCRIPTION

Figure 1:
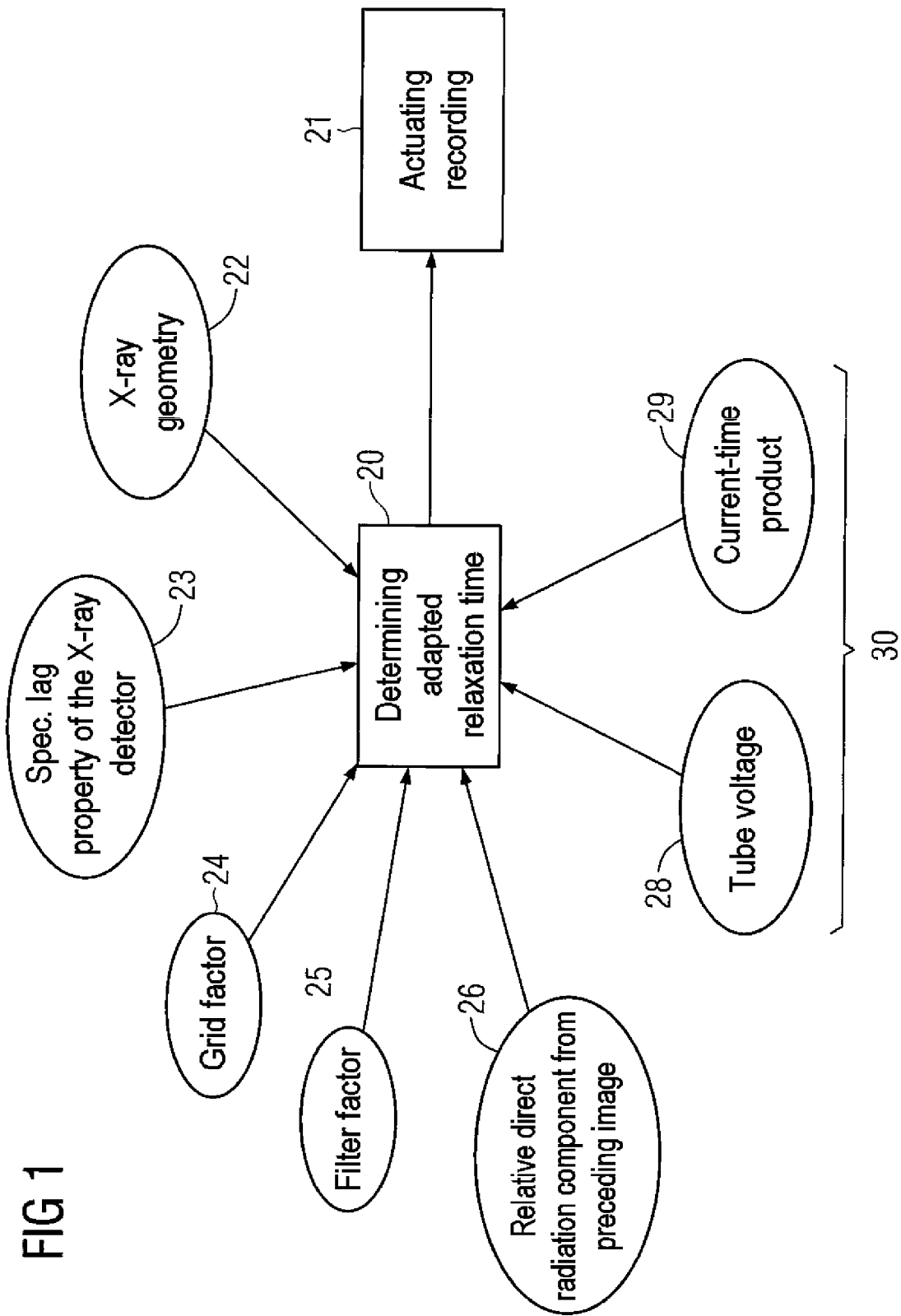
FIG. 1 shows a sequence of a method according to various embodiments.

As stated above, according to various embodiments, a method for recording an X-ray image using an X-ray system comprising an X-ray detector, an X-ray source (X-ray tube), a system control, and a computational unit, may comprise the following steps: determining a relaxation time, during which a ghosting effect of the X-ray detector resulting from a preceding X-ray image, more particularly a reference X-ray image, decays at least in part, which relaxation time is adapted to the X-ray image to be recorded, using information relating to the relative direct radiation component in a reference X-ray image and information relating to the recording geometry utilized for the reference X-ray image and/or the utilized primary X-ray dose (the tube voltage $kV_p$ and the current-time product mAs of the X-ray tube) and/or the utilized filtering; and utilizing the determined relaxation time to actuate the recording of the X-ray image to be recorded.

The method according to various embodiments allows largely ghost-free X-ray images to be recorded in minimal time and without complicated post-processing. This leads to an improved X-ray image quality and hence, in end effect, to a particularly good and reliable diagnosis being made.

Calculating an adapted relaxation time affords the possibility of optimally exploiting the natural relaxation of physical processes that lead to ghosting. In particular, the combined use of information relating to the relative direct radiation component and, supplementing this, the use of X-ray parameters (such as e.g. information relating to the recording geometry and/or the utilized primary X-ray dose and/or the filtering) from the preceding X-ray recording or a reference X-ray recording is very advantageous and minimizes the relaxation time. Exclusive use of the information relating to the relative direct radiation proportion can lead to determining an unnecessarily long relaxation time in certain circumstances, for example in the case of a clinically frequent, only weak over-irradiation, because the direct radiation identification signalizes the risk of a ghost image.

Exclusive use of the X-ray parameters can lead to determining an unnecessarily long relaxation time in certain circumstances, e.g. in the case of a high primary X-ray dose (which, e.g. does not impinge directly onto the X-ray detector, but is absorbed by the patient). Thus, the substantial advantage according to various embodiments lies precisely in using at least these two items of information. Additional information relating to the X-ray detector, more particularly the specific lag property of the detector system, as according to one embodiment, allows further minimization of the relaxation time with simultaneous ghosting avoidance. Additionally, further acceptance thresholds (e.g. from the field of physiologically perceptible ghost amplitudes) may contribute to the adjustment.

The information is advantageously evaluated by means of the computational unit and the adapted relaxation time is calculated therefrom. By way of example, the computational unit may be formed by a PC; the system control may moreover also be formed by a PC, more particularly the same PC. It is additionally possible for information and calculated data to be stored in a storage unit.

According to one embodiment, the adapted relaxation time is utilized as the pause between the recording of two X-ray images, more particularly between the recording of the preceding X-ray image and the X-ray image to be recorded.

According to a further embodiment, the reference X-ray image is formed by the respective preceding X-ray image. This affords the possibility of extracting information relating to the relative direct radiation component and the utilized X-ray parameters from a first X-ray image directly after it is recorded; this information can be utilized to calculate the adapted relaxation time and used directly as pause until a second X-ray image is recorded. Alternatively, it is possible for e.g. a first X-ray image to be recorded at the start of a series of images; information relating to the relative direct radiation component and the X-ray parameters can be extracted therefrom and utilized for calculating the adapted relaxation time. The calculated relaxation time is then used as pause in between the recording of two X-ray images for all subsequent X-ray images in the series.

By way of example, the information relating to the primary X-ray dose of the X-ray source can be formed by a tube voltage ($kV_p$) and/or a current-time product (mAs) of the X-ray tube utilized for the recording. The primary X-ray dose can be determined from the tube voltage and the current-time product. The information relating to the recording geometry can be formed by the mean distance between the X-ray detector and the focus of the X-ray source and/or by the central beam angle. The information relating to the filtering can be formed by an attenuation factor of an anti-scatter grid placed in front of the X-ray detector and/or a filter arranged on the X-ray tube (e.g. a Cu-filter).

When using X-ray tubes in X-ray technology, the following phraseology is conventional: The X-ray dose specifies the absorbed energy dE per unit mass at a particular point in a radiation field. The tuple $kV_p$ and mAs describes the emitted radiation field of the unfiltered X-ray tube in terms of energy distribution and energy fluence; it is also referred to as primary data of an X-ray recording taken under these conditions and documents the primary X-ray dose at which the recording was produced. The tube voltage $kV_p$, i.e. the maximum energy of the quanta emitted by an X-ray tube, in particular represents the energy distribution of the radiation field and hence represents the basic structure of the subsequent X-ray absorption image in the X-ray detector. However, it is also precisely in this energy distribution where the nonlinear component of this variable in the emitted energy fluence (and hence, again, in the X-ray dose) of the X-ray radiation is found. A small increase in the tube voltage results in a large increase in the X-ray dose. The beam current mA represents the emitted photon flux (photon fluence) and is linearly related to the dose power (i.e. the X-ray dose per unit time). The current-time product mAs is a variable that is linear in terms of the X-ray dose.

According to a further embodiment, the adapted relaxation time t is calculated using the formula $$t \propto D \oplus r_D \otimes l,$$

where D is the detector dose (i.e. the X-ray dose impinging on the X-ray detector), $r_D$ is the relative direct radiation component of the reference X-ray image, and l is the specific lag property of the X-ray detector. The operators represent $\oplus$ additive and $\otimes$ subtractive operators.

According to a further embodiment, the detector dose is calculated using the formula $$D \propto kV_p \oplus mAs \otimes gr \otimes fi \otimes ffA \otimes \alpha,$$

where $kV_p$ is the tube voltage of the X-ray source, mAs is the current-time product of the X-ray source, gr is the grid factor of a grating (e.g. anti-scatter grid), fi is the filter factor of a filter, ffA is the distance between the X-ray detector and the focus of the X-ray source, and $\alpha$ is the central beam angle.

Advantageously, a relaxation time is determined for a particularly optimized recording process, during which relaxation time the ghosting effect of the X-ray detector decays by at least 50%, more particularly by 90%.

The X-ray system according to various embodiments for carrying out the method comprises an X-ray detector, an X-ray source (X-ray tube), a system control, and a computational unit, wherein the computational unit is embodied to determine a relaxation time, during which a ghosting effect of the X-ray detector resulting from a preceding X-ray image decays at least in part, using information relating to the relative direct radiation component in a reference X-ray image and information relating to the utilized recording geometry and/or the primary X-ray dose of the X-ray source and/or the utilized filtering, which relaxation time is adapted to the X-ray image to be recorded, and the system control is embodied to utilize the determined relaxation time for actuating the recording of the X-ray image.

FIG. 1 shows the method according to various embodiments for recording an X-ray image. The method prevents the so-called ghosting from having a negative influence on the X-ray imaging. In a first step 20, a relaxation time, during which a ghosting effect of the X-ray detector resulting from a preceding X-ray image decays at least in part, for example by 50%, preferably by 90% or even by 99%, is determined, which relaxation time is adapted to the X-ray image to be recorded. By way of example, the determination can be brought about as a calculation by means of a system control (system control computer). Various data is utilized to determine the adapted relaxation time. Use is made of data relating to the relative direct radiation component 26 in a reference X-ray image, more particularly the or a preceding X-ray image (i.e. the or an X-ray image recorded previously). Moreover, use is made of X-ray parameters such as, for example, the tube voltage 28 or the current-time product 29 or information relating to the recording geometry 22 or the filters to be utilized, for example the filter factor 25 of an X-ray filter or the grid factor 24 of an anti-scatter grid, at the time of the recording of the reference X-ray image or the preceding X-ray image. Additionally, use can also be made of the specific lag property 23 of the X-ray detector.

In order to avoid ghosting, the method according to various embodiments explicitly proceeds from the system state and hence from optimizing the pause between two recordings. In order to determine the relaxation time, use is made of the natural, in particular exponential, relaxation of the physical processes that lead to ghosting.

The data relating to the relative direct radiation component 26 is obtained on the basis of, for example, the or a preceding X-ray image. The reference X-ray image or the preceding X-ray image should, where possible, be or have been recorded proceeding from a completely relaxed detection system. A relative evaluation of the direct radiation components is carried out on the corresponding raw image, for example by means of a histogram analysis, and this is stored in e.g. the header of the X-ray image.

With the aid of the relative evaluation of the direct radiation components, the system control decides, for example by means of a criterion based on bounds, whether areas of the X-ray detector were hit by direct radiation during the recording of the reference X-ray image and whether there is a risk of ghosting in the subsequent X-ray images. Moreover, a spatial reference of this direct radiation in various areas of the X-ray detector can also be evaluated. By way of example, from an applicative point of view, the bounds of the direct radiation identification in the central area of the detector can thus be lowered in relation to the edge areas in order to increase the sensitivity with respect to "overloading". However, determining the ghost-image intensity merely from the overloading of single pixels or a number of connected pixels of the X-ray detector is prone to errors because the overloading in this area may have only just lain outside the control range, or else it may be many orders of magnitude over said range. It is for this reason that the known data of the primary radiation of the preceding detector image is used to determine the relaxation time; that is to say use is made of e.g. the recording geometry, the primary X-ray dose of the X-ray source and/or the filtering. Together with these, it is then possible to deduce the intensity of the ghosting and hence the necessary optimum pause.

By way of example, an algorithm for determining the adapted relaxation time can be the following:

$$t \propto D \oplus r_D \otimes l,$$

where t is the relaxation time, D is the detector dose (i.e. the proportion of the X-ray dose actually impinging on the X-ray detector), $r_D$ is the relative direct radiation component of the reference X-ray image, and l is the specific lag property of the utilized X-ray detector. The operators represent $\oplus$ additive and $\otimes$ subtractive operators.

The use of the specific lag tendency of the utilized X-ray detector can be advantageous because even X-ray detectors of the same type can show variations in the relevant physical parameters. The image lag of an X-ray detector should be understood as meaning an incomplete deletion of an X-ray image in the X-ray detector after the readout.

The detector dose on the X-ray detector responsible for the direct radiation can be approximated as per the so-called exposure point scale (EP scale) from the $kV_p$ (tube voltage) and mAs (current-time product; the current-time product is determined by the set tube current in mA and the switching time in s) values. The recording geometry, i.e., for example, the distance between the X-ray source and X-ray detector as per the quadratic distance law, and/or a possible angle between the two (central beam angle), may likewise be used because these also have an influence on the direct radiation dose at the X-ray detector. Moreover, e.g. a Cu-filter, inserted by motorized means, at the output of the X-ray source damps the detector dose; moreover, the attenuation factor of an anti-scatter grid, possibly placed in front of the X-ray detector, may also be taken into account. Thus, an algorithm for determining the detector dose can be the following:

$$D \propto kV_p \oplus mAs \otimes gr \otimes fi \otimes ffA \otimes \alpha,$$

where $kV_p$ is the tube voltage of the X-ray source, mAs is the current-time product of the X-ray source, gr is the grid factor of a grating (e.g. an absorption grating such as the anti-scatter grid), fi is the filter factor of a filter (e.g. a Cu-filter), ffA is the distance between the X-ray detector and the focus of the X-ray source, and a is the central beam angle.

Moreover, it is also possible to define a further threshold that specifies the relative amount of a ghost image from the preceding image that may be accepted in an X-ray image to be recorded. By way example, maximum ghost-image components of 50%, 10% or, for a particularly good X-ray image, even 1% may be provided in this case.

Figure 2:
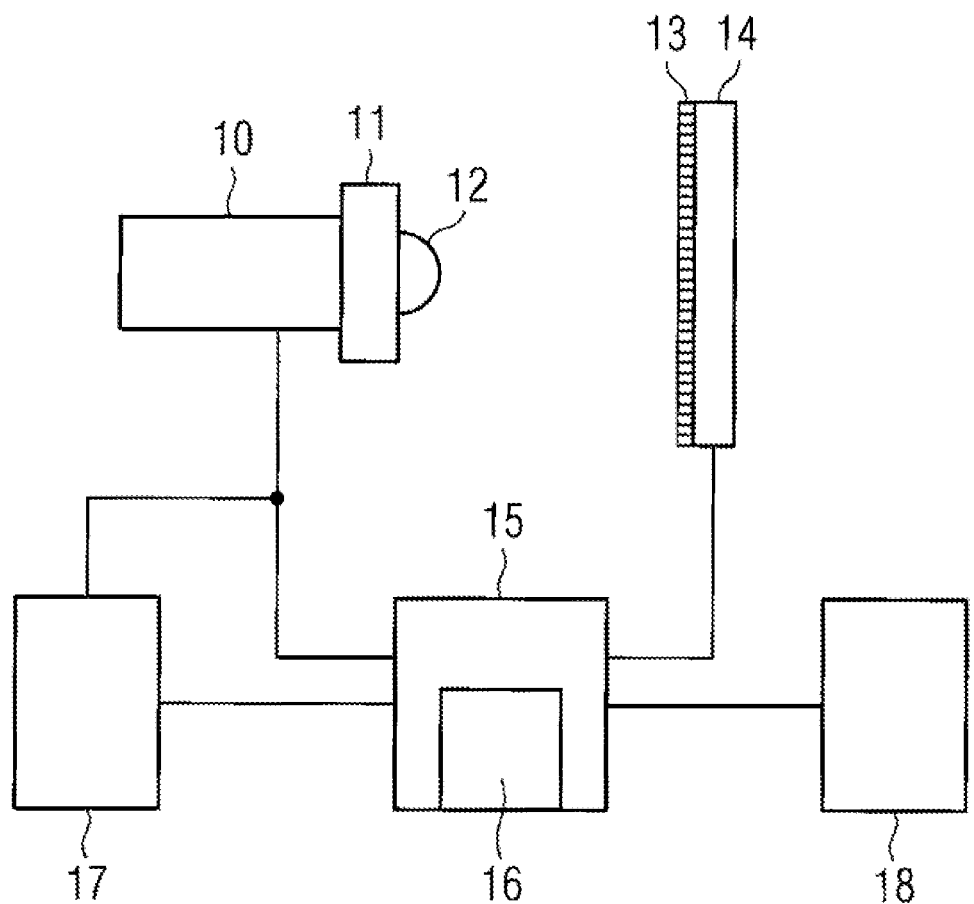
FIG. 2 shows a view of an X-ray system that is suitable for carrying out the method.

FIG. 2 shows a schematic design of an X-ray system that is suitable for carrying out the method. The X-ray system has an X-ray emitter 10 as an X-ray source for generating X-ray radiation and an X-ray detector 14 for detecting the X-ray radiation. A collimator 11 and a filter 12, for example a Cu-filter, are placed in front of the X-ray emitter 10; the high voltage is produced by a generator 17. An anti-scatter grid 13 for removing scattered radiation is arranged in front of the X-ray detector 14. The X-ray system is actuated by a system control 15; moreover, there is a computational unit 16, wherein system control 15 and computational unit 16 may be formed by a PC. Moreover, there is an image system 18 for the further processing of X-ray images. The computational unit calculates the adapted relaxation time, as specified above, from the appropriate parameters and can for example store said time. The calculated relaxation time is used by the system control for actuating the pause in between the recording of two X-ray images. Thus, for example, after a recording has taken place, the triggering of a further X-ray pulse may be blocked for the duration of the relaxation time.

Overall, a new pause may be established at regular intervals, for example after each individual X-ray recording or after a number of X-ray recordings or at regular time intervals or if at least one X-ray parameter (such as tube voltage, recording geometry . . . ) is modified. As a result of this, the timing in X-ray recordings with good recording quality is always set in an optimum fashion.

In summary: In order to optimize the recording time, provision is made for a method for recording an X-ray image using an X-ray system, comprising an X-ray detector, an X-ray source, a system control, and a computational unit, wherein information relating to the relative direct radiation component in a reference X-ray image and information relating to the recording geometry utilized for the reference X-ray image and/or the primary X-ray dose utilized for the reference X-ray image and/or the filtering utilized for the reference X-ray image is used to determine a relaxation time, during which a ghosting effect of the X-ray detector resulting from a preceding X-ray image, more particularly the reference X-ray image, decays at least in part, which relaxation time is adapted to the X-ray image to be recorded, and the determined relaxation time is utilized to actuate the recording of the X-ray image.

What is claimed is:

1. A method for recording an X-ray image using an X-ray system, comprising an X-ray detector, an X-ray source, a system control, and a computational unit, the method comprising:

using information relating to a relative direct radiation component in a reference X-ray image and information relating to at least one of:

the recording geometry utilized for the reference X-ray image;

the primary X-ray dose utilized for the reference X-ray image; and the filtering utilized for the reference X-ray image, for determining a relaxation time, during which a ghosting effect of the X-ray detector resulting from a preceding X-ray image decays at least in part, which relaxation time is adapted to the X-ray image to be recorded, wherein the adapted relaxation time t is calculated using the formula:

$$t \propto D + r_D - 1$$

where D is the detector dose, $r_D$ is the relative direct radiation component of the reference X-ray image, and l is the specific lag property of the X-ray detector; and utilizing the adapted relaxation time to actuate the recording of the X-ray image.

2. The method according to claim 1, wherein the preceding X-ray image is the reference X-ray image.

3. The method according to claim 1, wherein information relating to the X-ray detector is likewise used for determining the adapted relaxation time.

4. The method according to claim 1, wherein the information is evaluated by means of the computational unit and the adapted relaxation time is calculated therefrom.

5. The method according to claim 1, wherein the adapted relaxation time is utilized as the pause between the recording of two X-ray images.

6. The method according to claim 5, wherein the adapted relaxation time is utilized as the pause between the recording of the preceding X-ray image and the X-ray image to be recorded.

7. The method according to claim 1, wherein an evaluation of the reference X-ray image in respect of direct radiation components is utilized to determined the adapted relaxation time.

8. The method according to claim 1, wherein the reference X-ray image is formed by the respective preceding X-ray image.

9. The method according to claim 1, wherein the information relating to the primary X-ray dose from the X-ray source comprises at least one of a tube voltage and a current-time product.

10. The method according to claim 1, wherein the information relating to the recording geometry comprises a distance between the X-ray detector and the focus of at least one of the X-ray source and a central beam angle.

11. The method according to claim 1, wherein the information relating to the filtering comprises an attenuation factor of at least one of an anti-scatter grid and a filter.

12. The method according to claim 2, wherein the information relating to the X-ray detector comprises a specific lag property of the X-ray detector.

13. The method according to claim 1, wherein the detector dose is calculated using the formula $$D \propto kV_p + mAs - gr - fi - ffA - \alpha,$$

where $kV_p$ is the tube voltage of the X-ray source, mAs is the current-time product of the X-ray source, gr is the grid factor of a grating, fi is the filter factor of a filter, ffA is the distance between the X-ray detector and the focus of the X-ray source, and $\alpha$ is the central beam angle.

14. The method according to claim 1, wherein a relaxation time is determined, during which a ghosting effect of the X-ray detector decays by at least 50%, more particularly by 90%.

15. An X-ray system for recording an X-ray image, comprising:
   an X-ray detector,
   an X-ray source,
   a system control, and
   a computational unit, wherein the computational unit is embodied to determine a relaxation time, during which a ghosting effect of the X-ray detector resulting from a preceding X-ray image decays at least in part, using information relating to the relative direct radiation component in a reference X-ray image and information relating to at least one of:
      the recording geometry utilized for the reference X-ray image,
      the utilized primary X-ray dose, and
      the utilized filtering,
   which relaxation time is adapted to the X-ray image to be recorded,
   wherein the adapted relaxation time t is calculated using the formula:

$$t \propto D + r_D - 1$$

where D is the detector dose, $r_D$ is the relative direct radiation component of he reference X-ray image, and I is the specific lag property of the X-ray detector; and
   the system control is embodied to utilize the determined relaxation time for actuating the recording of the X-ray image.

16. The X-ray system according to claim 15, wherein information relating to the X-ray detector is likewise used for determining the adapted relaxation time.

17. The X-ray system according to claim 15, wherein the information is evaluated by means of the computational unit and the adapted relaxation time is calculated therefrom.

18. The X-ray system according to claim 15, wherein the adapted relaxation time is utilized as the pause between the recording of two X-ray images.

19. The X-ray system according to claim 15, wherein an evaluation of the reference X-ray image in respect of direct radiation components is utilized to determined the adapted relaxation time.

* * * * *